(12) United States Patent
Dezawa et al.

(10) Patent No.: US 7,718,429 B2
(45) Date of Patent: May 18, 2010

(54) METHOD FOR INDUCING DIFFERENTIATION TO SKELETAL MUSCLE CELLS

(75) Inventors: Mari Dezawa, Kyoto (JP); Yo-ichi Nabeshima, Kyoto (JP); Mikio Hoshino, Kyoto (JP)

(73) Assignee: Kyoto University, Kyoto (JP)

( * ) Notice: Subject to any disclaimer, the term of this patent is extended or adjusted under 35 U.S.C. 154(b) by 0 days.

(21) Appl. No.: 11/722,602

(22) PCT Filed: Dec. 22, 2005

(86) PCT No.: PCT/JP2005/023598
§ 371 (c)(1),
(2), (4) Date: Oct. 11, 2007

(87) PCT Pub. No.: WO2006/068225
PCT Pub. Date: Jun. 29, 2006

(65) Prior Publication Data
US 2008/0113435 A1 May 15, 2008

(30) Foreign Application Priority Data
Dec. 24, 2004 (JP) .............................. 2004-372656

(51) Int. Cl.
*C12N 5/00* (2006.01)
*C12N 5/02* (2006.01)
*C12N 5/07* (2010.01)
*C12N 5/10* (2006.01)

(52) U.S. Cl. ..................... 435/377; 435/375; 435/372; 435/355; 435/325

(58) Field of Classification Search ................ 435/377
See application file for complete search history.

(56) References Cited

U.S. PATENT DOCUMENTS

2006/0166362 A1 7/2006 Dezawa et al.

FOREIGN PATENT DOCUMENTS

EP   1 479 767    11/2004
JP   2003-144155   5/2003

OTHER PUBLICATIONS

Schuldiner, M et al, 2000, PNAS, 97:11307-11312.*
Rickman, SW et al. 2001, Soc. Neurosci. Abstracts, 27:58.*
Deng, W et al, 2001, Biochem Biophys Res Comm, 282:148-152.*
Hicok, KC et al., Journal of Bone and Mineral Res., vol. 13, pp. 205-217.*
Higuchi, 1995, Molecular Brain Research, 29:263-272.*
Neves, H et al., 2006, Stem Cells, 24:1328-1337.*
Varnum-Finney, 1998, Blood, 91:4084-4091.*
Li et al , 1998, Immunity, 8:43-55.*
Dezawa et al., "Specific Induction of Neuronal Cells from Bone Marrow Stromal Cells and Application for Autologous Transplantation" *Journal of Clinical Investigation* 113(12):1701-10, 2004.
Li et al., "The Human Homolog of Rat *Jagged1* Expressed by Marrow Stroma Inhibits Differentiation of 32D Cells Through Interaction with Notch1" *Immunity* 8:43-55, 1998.
Dezawa., "Insights into Autotransplantation: The Unexpected Discovery of Specific Induction Systems in Bone Marrow Stromal Cells" *Cellular and Molecular Life Sciences* 63(23):2764-72, 2006.
Lindsell et al., "Jagged: A Mammalian Ligand that Activates Notch 1" *Cell* 80(6):909-17, 1995.
Yoshida et al., "Cell Heterogeneity Upon Myogenic Differentiation: Down-Regulation of MyoD and Myf-5 Generates 'Reserve Cells'" *Journal of Cell Science* 111:769-79, 1998.
Luo et al., "Isolation and Functional Analysis of a cDNA for Human *Jagged2*, a Gene Encoding a Ligand for the Notch1 Receptor" *Molecular and Cellular Biology* 17(10):6057-6067, 1997.
Doi, H. et al. Notch Ligand Jagged1 Induced Differentiation of Vascular Smooth Muscle Cells through RPB-Jk- Dependent Mechanisms in Mesenchymal Cells, *Circulation*, Oct. 2005, vol. 112, No. 17, Suppl. S, pp. U122.
Dezawa, M. et al. Bone Marrow Stomal Cells Generate Muscle Cells and Repair Muscle Degeneration, *Science* Jul. 8, 2005, vol. 309, pp. 314-317.
English language abstract of JP 2003-144155.

* cited by examiner

*Primary Examiner*—Valarie Bertoglio
(74) *Attorney, Agent, or Firm*—Greenblum & Bernstein, P.L.C.

(57) ABSTRACT

A method of efficiently and conveniently inducing differentiation from bone marrow stromal cells to skeletal muscle cells, which comprises the steps of: (a) the step of adding one or more kinds of substances selected from the group consisting of a cyclic AMP increasing agent, a cAMP analogue, and a cell differentiation stimulating factor to a culture of bone marrow stromal cells, wherein said bone marrow stromal cells are not treated with a demethylating agent, and culturing the cells; (b) the step of introducing a Notch gene and/or a Notch signaling related gene into the cells obtained in the step (a), and culturing the cells to obtain a culture of myoblasts, provided that said culture does not contain the cells introduced with the gene and non-introduced cells; and (c) the step of adding a Notch ligand to the culture of myoblasts obtained in the step (b), and culturing the cells.

5 Claims, No Drawings

METHOD FOR INDUCING DIFFERENTIATION TO SKELETAL MUSCLE CELLS

TECHNICAL FIELD

The present invention relates to a method for inducing differentiation from bone marrow stromal cells to skeletal muscle cells.

BACKGROUND ART

For muscular diseases, especially degenerative diseases of skeletal muscles such as muscular dystrophy, no effective therapeutic means is available at present. If skeletal muscle cells can be prepared from patient's own bone marrow stromal cells, autologous transplantation becomes possible, which is believed to be an effective therapeutic method. Moreover, utilization of skeletal muscle cells generated from patient's own bone marrow stromal cells is expected not only in therapeutic aspects such as the aforementioned regeneration medicine, but in engineering aspects such as artificial organs with prospect of future development. Since muscle cells can be easily prepared by a culture level procedure, use of the cells is also expected in preparation of hybrid type artificial organs and the like.

As a method for inducing differentiation of bone marrow stromal cells into skeletal muscle cells, the method disclosed in Japanese Patent Unexamined Publication (KOKAI) No. 2003-144155 is known. This method comprises, as essential steps, (1) the step of isolating bone marrow stromal cells from bone marrow and culturing the cells; (2) the step of adding a demethylating agent (5-azacytidine); (3) the step of adding a cAMP-increasing agent or a cAMP analogue (forskolin), and/or a cell differentiation stimulating factor (bFGF, PDGF-AA, Heregulin); (4) the step of introducing a Notch gene and/or a Notch signaling related gene into the cells and culturing the cells; (5) the step of co-culturing said gene-introduced cells with non-introduced cells; and (6) the step of adding a cAMP-increasing agent or a cAMP analogue (forskolin).

However, the aforementioned method includes six steps, and thus has a problem that operations are very complicated. If multiple steps with complicated operations are performed, indefinite factors increases, which may lead to decrease in induction efficiency. Moreover, this method is basically proposed as a method for inducing differentiation into nerve cells, and is not optimized for selectively inducing differentiation into skeletal muscle cells. Furthermore, this method uses a mixture system containing elements other than myocytes, and therefore, the method has a problem from a viewpoint of safety for clinical application of induced skeletal muscle cells.

DISCLOSURE OF THE INVENTION

Object to be Achieved by the Invention

An object of the present invention is to provide a method for inducing differentiation from marrow stromal cells to skeletal muscle cells. More specifically, the object of the present invention is to provide a method for more efficiently and conveniently inducing differentiation from bone marrow stromal cells to skeletal muscle cells with good reproducibility compared with the method disclosed in Japanese Patent Unexamined Publication No. 2003-144155.

Means for Achieving the Object

The inventors of the present invention conducted various researches to achieve the aforementioned object. As a result, they found that, in the induction of differentiation of bone marrow stromal cells into skeletal muscle cells, (2) the step of adding a demethylating agent (5-azacytidine), (5) the step of co-culturing gene-introduced cells with non-introduced cells; and (6) the step of adding a cAMP-increasing agent or a cAMP analogue (forskolin), which steps are considered as essential in the method disclosed in Japanese Patent Unexamined Publication No. 2003-144155, were successfully omitted, thereby the operations of the total process were simplified to markedly increase differentiation inducing efficiency and efficiently create skeletal muscle cells. The present invention was accomplished on the basis of the aforementioned finding.

The present invention thus provides a method for inducing differentiation of bone marrow stromal cells to skeletal muscle cells, which comprises the following steps:

(a) the step of adding one or more kinds of substances selected from the group consisting of a cyclic AMP (henceforth also abbreviated occasionally as "cAMP") increasing agent, a cAMP analogue, and a cell differentiation stimulating factor to a culture of bone marrow stromal cells wherein said bone marrow stromal cells are cells not treated with a demethylating agent, and culturing the cells;

(b) the step of introducing a Notch gene and/or a Notch signaling related gene into the cells obtained in the aforementioned step (a), and culturing the cells to obtain a culture of myoblasts wherein said culture does not contain a co-culture of the cells introduced with the gene and non-introduced cells; and (c) the step of adding a Notch ligand to the culture of myoblasts obtained in the aforementioned step (b), and culturing the cells.

According to preferred embodiments of the aforementioned invention, provided are the aforementioned method, wherein Jagged 1 protein is used as the Notch ligand in the step (c); and the aforementioned method, wherein the step (c) is performed in a serum free medium.

From another aspect, the present invention provides a method for inducing differentiation of bone marrow stromal to myoblasts, which comprises the following steps:

(a) the step of adding one or more kinds of substances selected from the group consisting of a cyclic AMP increasing agent, a cAMP analogue, and a cell differentiation stimulating factor to a culture of bone marrow stromal cells wherein said bone marrow stromal cells are cells not treated with a demethylating agent, and culturing the cells; and (b) the step of introducing a Notch gene and/or a Notch signaling related gene into the cells obtained in the aforementioned step (a), and culturing the cells wherein said culture does not contain a co-culture of the cells with the genes and non-introduced cells.

From a still further aspect, the present invention provides a method for inducing differentiation of myoblasts to skeletal muscle cells, which comprises the step of adding a Notch ligand to a culture of myoblasts, and culturing the cells.

The present invention also provides skeletal muscle cells or myoblasts obtainable by the aforementioned methods, a pharmaceutical composition for therapeutic treatment of a muscular disease, which comprises the aforementioned skeletal muscle cells or myoblasts, and use of the aforementioned skeletal muscle cells or myoblasts for the manufacture of the aforementioned pharmaceutical composition. The present invention further provides a method for therapeutic treatment of a muscular disease, which comprises administering a therapeutically effective amount of skeletal muscle cells or myoblasts obtainable by the aforementioned methods to a patient in need of administration of skeletal muscle cells or myoblasts by local administration or systemic administration; and the aforementioned method, wherein the skeletal muscle cells or myoblasts are cells induced by differentiation of patient's autologous or heterologous bone marrow stromal cells.

BEST MODE FOR CARRYING OUT THE INVENTION

The method of the present invention is a method for inducing differentiation of bone marrow stromal cells to skeletal muscle cells, which comprises the following steps:

(a) the step of adding one or more kinds of substances selected from the group consisting of a cAMP increasing agent, a cAMP analogue, and a cell differentiation stimulating factor to a culture of bone marrow stromal cells wherein said bone marrow stromal cells are cells not treated with a demethylating agent, and culturing the cells;

(b) the step of introducing a Notch gene and/or a Notch signaling related gene into the cells obtained in the aforementioned step (a), and culturing the cells to obtain a culture of myoblasts, provided that said culture does not contain a co-culture of the gene-introduced cells and non-introduced cells; and (c) the step of adding a Notch ligand to the culture of myoblasts obtained in the aforementioned step (b), and culturing the cells.

The method of the present invention is characterized by not including the steps mentioned as essential steps in the previously published method for inducing differentiation to skeletal muscle cells (the method comprising the six steps described in the aforementioned patent publication, paragraph [0022] and the like): (2) the step of adding a demethylating agent (5-azacytidine), (5) the step of co-culturing of the cells introduced with the gene and non-introduced cells; and (6) the step of adding a cAMP-increasing agent or a cAMP analogue (forskolin). In particular, not including the co-culture of the cells introduced with the gene and the non-introduced cells is a primary characteristic of the method of the present invention. Although the method of the present invention can be used for the preparation of skeletal muscle cells of mammals including human, a preferred object is human. Details of each step according to the present invention can be better understood by referring to Japanese Patent Unexamined Publication No. 2003-144155 mentioned above. The entire disclosure of said patent publication is incorporated by reference into the disclosures of the specification.

The bone marrow stromal cells used in the method of the present invention mean cells present in the bone marrow other than cells of the hemopoietic system, and they are considered to be potentially differentiable into osteocytes, chondrocytes, adipocytes and the like. Bone marrow stromal cells are identified by positivity (+) for Thy1 and 2, positivity (+) for β1-integrin, and negativity (−) for CD34. A preparation method of bone marrow stromal cells is specifically explained in detail in Japanese Patent Unexamined Publication No. 2003-144155, those skilled in the art can easily obtain bone marrow stromal cells. For example, culture of bone marrow stromal cell can be prepared by extracting bone marrow stromal cell from the bone marrow, and culturing the cells in a standard basal medium supplemented with serum. For example, it is desirable to subculture bone marrow stromal cells for 3 to 4 generations, and then prepare a culture adjusted to a cell density of, for example, about 1700 cells/cm$^2$. As the standard basal medium, Eagle's alpha modified minimum essential medium and the like can be used, and as the serum, fetal bovine serum, or in the case of human, human serum can be used. The bone marrow stromal cells used in the method of the present invention need not be treated with the demethylating agent employed in the method described in Japanese Patent Unexamined Publication No. 2003-144155. One of the characteristics of the present invention is based on the finding that induction of differentiation to skeletal muscle cells were efficiently achievable if the treatment with the demethylating agent is omitted, which is conventionally considered essential.

As the cAMP increasing agent or the cAMP analogue, for example, forskolin can be used, but not limited thereto. One or more kinds of cAMP increasing agents or cAMP analogues can be appropriately used. Although a concentration of the cAMP increasing agent or the cAMP analogue is not particularly limited, the concentration may be, for example, about 0.001 nM to 100 μM, preferably about 500 nM to 50 μM. As the cell differentiation stimulating factor, for example, basic fibroblast growth factor (bFGF), platelet-derived growth factor-AA (PDGF-AA), neuregulin (trade name: Heregulin), and the like can be used, and two or more kinds of these substances may be used in combination. Although a concentration of the cell differentiation stimulating factor is not particularly limited, the concentration may be, for example, about 0.001 ng/ml to 100 μg/ml, preferably about 0.5 ng/ml to 2 μg/ml. It is also preferable to use the cell differentiation stimulating factor in combination with the cAMP increasing agent or the cAMP analogue. For example, forskolin (5 μM), bFGF (10 ng/ml), PDGF-AA (5 ng/ml) and neuregulin (200 ng/ml) are added to the MEM Eagle Modification medium containing 10% fetal bovine serum (FBS), and bone marrow stromal cells are cultured therein. Pax7 as a marker of skeletal muscle stem cells comes to be expressed in this stage, and by using the marker as an index, the addition of the aforementioned agents and the culture can be performed.

Introduction of the Notch gene and/or Notch signaling related gene may be attained by, for example, lipofection using an expression vector for mammalian cells. However, the method is not limited to the above method, and a suitable gene introduction means can be employed. For example, the pCI-neo-NICD plasmid containing the Notch cytoplasm domain (NICD) cDNA (plasmid described in Japanese Patent Unexamined Publication No. 2003-144155, Example 1) can be introduced. After the aforementioned gene introduction, cells introduced with the gene can be preferably selected. This selection can be performed, for example, on the basis of neomycin resistance by adding G418 sulfate, and usually completed in about 10 to 14 days. The selected cells are desirably cultured until they reach 100% confluence. The cells obtained as described above constitute a myoblast population, and the cells are transformed so that transcription factors as skeletal muscle markers such as MyoD and myogenin come to be detectable. After the gene introduction or the aforementioned selection, the method described in Japanese Patent Unexamined Publication No. 2003-144155 employs the step of coculture of the cells after introduction with the gene and cells not introduced with the gene. Whilst, the aforementioned co-culture is not carried out in the method of the present invention. Another characteristic of the present invention is based on the finding that efficient differentiation to skeletal muscle cells was successfully induced if the aforementioned co-culture is omitted, which is conventionally considered essential. Therefore, in the method of the present invention, after the aforementioned gene introduction or the aforementioned selection, the step (c) is performed without performing the co-culture.

Then, fusion induction for inducing mature skeletal muscle cells from the resulting myoblasts is performed according to the step (c). This step can be performed by adding a Notch ligand to the culture of myoblasts and culturing the cells. As the Notch ligand, for example, Jagged 1 protein (Lindsell, C. E. et al., Cell, 80, pp. 909-917, 1995) can be used. Although a concentration of Jagged 1 protein is not particularly limited, the concentration may be, for example, about 1 to 20 µg/ml, preferably about 5 µg/ml. A type of the medium is not particularly limited, and an ordinary basal medium, for example, MEM Eagle modification medium and the like can be used. Although about 10% of serum such as FBS can be added to the medium, a serum free medium can be preferably used. By using, for example, a serum free medium such as TTS-serum free medium (Yoshida, N. et al., J. Cell Sci., 111, pp. 769-779, 1998), skeletal muscle cells suitable for clinical application can be prepared. As a result of the aforementioned fusion induction, polynuclear skeletal muscle cells expressing mature markers such as Myf6/MRF4 and positive to the myosin heavy chain and skeletal myosin are induced. These skeletal muscle cells show spontaneous constriction movements during the culture. In the method described in Japanese Patent Unexamined Publication No. 2003-144155, cells after introduction with the gene and the cells not introduced with the gene are co-cultured, and then the cAMP increasing agent or the cAMP analogue is added to the culture to induce differentiation into mature skeletal muscle cells. However, in the method of the present invention, it is not necessary to add the cAMP increasing agent or the cAMP analogue to the culture. A still further characteristic of the present invention is based on the finding that differentiation to functionally sufficient matured skeletal muscle cells was successfully induced if addition of the cAMP-increasing agent or cAMP analogue is omitted, which is conventionally considered essential.

Then, the skeletal muscle cells can be cloned by performing limiting dilution of the resulting culture of the skeletal muscle cells to a density of 1 cell per well, and a population of polynuclear skeletal muscle cells having the constriction ability can be obtained again from the living clones, which are usually obtained at a ratio of about 90%. The resulting cell population is a population substantially purely consisting of muscle cells, and not containing any other elements, and can be preferably used, in particular, for a purpose of therapeutic treatment of a muscular disease and the like. Furthermore, the resulting cell population contains skeletal muscle stem cells, and muscle cells can be stably prepared therefrom even after multiple times of subculture.

The skeletal muscle cells obtained by the method of the present invention can be used for, for example, local or systemic administration to a patient with a muscular disease such as muscular dystrophy; muscle supplementation for muscle loss or damage at the time of traffic injury, thermal burn and the like; muscle reconstruction in a patient of disuse muscular atrophy due to a cerebrovascular disease, spinal cord injury or neurodegenerative disease; therapeutic treatment of muscular atrophy accompanying nerve damages such as brachial plexus paralysis, and the like. However, the uses of the skeletal muscle cells obtained by the present invention are not limited to the specific uses exemplified above. For example, skeletal muscle cells can be prepared according to the method of the present invention by using bone marrow stromal cells extracted from a patient, and they can be autotransplanted to a lesion of the patient. Moreover, heterologous transplantation is also performable in a similar manner with a premise of HLA compatibility. The skeletal muscle cells obtained by the method of the present invention constitute a substantially pure skeletal muscle cell population containing stem cells, and when the cells are transplanted, the stem cells can be taken in vivo and regenerate skeletal muscle cells in response to repeated muscle damages, which is a great advantage for clinical applications.

EXAMPLES

The present invention will be more specifically explained with reference to the following examples. However, the scope of the present invention is not limited to the following examples.

Example 1

According to the method described in Japanese Patent Unexamined Publication No. 2003-144155, stromal cells were extracted from the bone marrow of muscular cell-induced adult rats (Wistar rats) and humans, and cultured. As a medium, Minimum Essential Medium (MEM) Eagle Modification (M4526, Sigma) containing 15% fetal bovine serum (14-501F, Lot #61-1012, Biowhittaker) was used. After the cells were subcultured to four generations, the cells reaching to 80 to 90% confluence were inoculated at a density of 1800 to 1900 cells/cm$^2$, and from the next day, the medium was changed to a medium supplemented with 5 µM of forskolin (344273, Calbiochem), 10 ng/ml of basic fibroblast growth factor (100-18B, Peprotech EC, Ltd.), 5 ng/ml of platelet-derived growth factor-AA (396-HB, Peprotech EC Ltd.) and 200 ng/ml of Heregulin (396-HB, R&D Systems), and the culture was continued for 3 days. Then, the gene of the Notch intracellular domain was introduced into the cells according to the method of Japanese Patent Unexamined Publication No. 2003-144155, Example 1.

On the next day after the introduction, G418 sulfate (83-5027, Gibco BRL) was added at a concentration of 200 ng/ml to select the introduced cells for 10 days. After restoration of the cell number reaching to substantially 100% confluence, 5 µg/ml of Jagged 1 protein (recombinant Rat Jagged 1/Fc chimera, 3599, GT TECHNE) was added to the MEM Eagle Modification medium containing 10% FBS, and the cells were cultured for 5 days to perform fusion induction. During the culture, the cells fused and polynuclear skeletal muscle cells locally appeared, which increased with passage of time, and thus polynuclear skeletal muscle cells positive to the myosin heavy chain and skeletal myosin were formed, whose spontaneous constriction movements were microscopically observable under the culture condition. In these cells, expression of the mature markers such as Myf6/MRF4 was confirmed. The induction efficiency into the skeletal muscle cells was about 40% on the 14th day of the fusion induction. When differentiation into skeletal muscle cells was induced as a control according to the method using the demethylation treatment, co-culture, and subsequent addition of forskolin described in Japanese Patent Unexamined Publication No. 2003-144155, the induction ratio into skeletal muscle cells was 20.8±3.5%.

Example 2

Differentiation into skeletal muscle cells was induced in the same manner as that in Example 1 mentioned above, provided that a serum free medium was used for the fusion induction. As the serum free medium, DMEM containing 10 μg/ml of insulin, 5 μg/ml of transferrin, 10 nmol of sodium selenite, 1 mg/ml of BSA, and 60 μg/ml of kanamycin (this medium is called "ITS-serum free medium") supplemented with Jagged 1 protein (recombinant Rat Jagged 1/Fc Chimera, 3599, GT TECHNE) at a final concentration of 5 μg/ml was used. As a result, the number of the polynuclear skeletal muscle cells was 16 per 35 mm culture dish on the first day of the culture, and 664 on the 5th day of the culture. Whilst when the cells were cultured in a medium consisting solely of the aforementioned serum free medium (without addition of Jagged 1 protein) as a control, the number was 13 on the 1st day of the culture, and 487 on the 5th day of the culture. From these results, it was demonstrated that differentiation into mature muscle cells was also successfully induced by the addition of Jagged 1 protein to a serum free medium.

INDUSTRIAL APPLICABILITY

The method of the present invention is simplified in the total steps compared with the method for inducing differentiation into skeletal muscle cells described in Japanese Patent Unexamined Publication No. 2003-144155, and skeletal muscle cells can be conveniently and efficiently prepared by the method of the present invention. According to the method of the present invention, differentiation into myoblasts serving as precursor cells of skeletal muscle cells can be induced by the step (b), and then differentiation of the myoblasts into mature skeletal muscle cells can be induced stepwise. Therefore, the differentiation stage, proliferation of cells, and the like can be controlled. Furthermore, the method of the present invention does not use a mixed system containing cells other than myoblasts or skeletal muscle cells, and is capable of efficiently preparing substantially pure skeletal muscle cell population. Therefore, skeletal muscle cells obtained can be used as a safe medicament for treatment of muscular diseases.

What is claimed is:

1. A method for inducing differentiation from bone marrow stromal cells to skeletal muscle cells, which comprises:
   (a) adding
      (i) a cyclic AMP (cAMP) increasing agent or a cAMP analogue, and
      (ii) a cell differentiation stimulating factor comprising bFGF, PDGF-AA, and neuregulin
   to a culture of bone marrow stromal cells wherein said bone marrow stromal cells are not treated with a demethylating agent, and culturing the cells;
   (b) introducing a Notch gene into the cells obtained in (a), and culturing the cells to obtain a culture of myoblasts, provided that said culture does not contain a co-culture of the cells introduced with the gene and non-introduced cells; and
   (c) adding a Notch ligand to the culture of the myoblasts obtained in (b), and culturing the cells such that skeletal muscle cells are induced.

2. The method according to claim 1, wherein the Notch ligand is Jagged 1 protein.

3. The method according to claim 1, wherein (c) is performed in a serum free medium.

4. A method for inducing differentiation from bone marrow stromal cells to myoblasts, which comprises:
   (a) adding
      (i) a cyclic AMP (cAMP) increasing agent or a cAMP analogue, and
      (ii) a cell differentiation stimulating factor comprising bFGF, PDGF-AA, and neuregulin
   to a culture of bone marrow stromal cells, wherein said bone marrow stromal cells are not treated with a demethylating agent, and culturing the cells; and
   (b) introducing a Notch gene into the cells obtained in (a), and culturing the cells, provided that said culture does not contain a co-culture of the cells introduced with the gene and non-introduced cells, such that myoblasts are induced.

5. The method according to claim 2, wherein (c) is performed in a serum free medium.

* * * * *